United States Patent
Skinner et al.

(10) Patent No.: US 8,403,917 B2
(45) Date of Patent: Mar. 26, 2013

(54) PNEUMATIC SURGICAL INSTRUMENT DETECTION SYSTEM

(75) Inventors: Allen W. Skinner, Chesterfield, MO (US); James T. Perkins, St. Charles, MO (US); David W. Hertweck, Valley Park, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 273 days.

(21) Appl. No.: 12/980,733

(22) Filed: Dec. 29, 2010

(65) Prior Publication Data

US 2012/0172849 A1 Jul. 5, 2012

(51) Int. Cl.
*A61B 17/00* (2006.01)
(52) U.S. Cl. ............................................. 606/1
(58) Field of Classification Search .................. 606/1, 4, 606/5, 6
See application file for complete search history.

(56) References Cited

U.S. PATENT DOCUMENTS

| 4,493,698 | A | * | 1/1985 | Wang et al. | 604/541 |
| 5,979,494 | A | * | 11/1999 | Perkins et al. | 137/487.5 |
| 2005/0025671 | A1 | * | 2/2005 | Kral et al. | 422/62 |
| 2011/0054508 | A1 | * | 3/2011 | Zhou et al. | 606/170 |

* cited by examiner

*Primary Examiner* — Henry M Johnson, III
*Assistant Examiner* — John R Downey
(74) *Attorney, Agent, or Firm* — Jeffrey B. Powers

(57) ABSTRACT

A system detects whether a pneumatic surgical instrument is attached to a surgical system. A drive valve has an input for connection to a source of pressurized air, an output for connection to the surgical instrument, and an exhaust for exhausting pressurized air during operation of the surgical instrument. A pressure transducer in communication with the exhaust senses a pressure profile of air flow from the exhaust. A first sensed pressure profile indicates that the surgical instrument is connected to the output and a second sensed pressure profile indicates that the surgical instrument is not connected to the output. A detection circuit connected to an output of the pressure transducer detects whether the surgical instrument is attached to the surgical system based on the sensed pressure profile.

10 Claims, 3 Drawing Sheets

PNEUMATIC SURGICAL INSTRUMENT DETECTION SYSTEM

FIELD

The present embodiment relates to surgical systems, and more particularly, to surgical systems having detection systems for determining whether a pneumatic surgical instrument is connected to the surgical system.

BACKGROUND

This section provides background information related to the present disclosure which is not necessarily prior art.

In performing surgery, such as ophthalmic surgery, where procedures are performed adjacent delicate tissue, like the retina, it is desirable to have detection mechanisms to ensure that surgical instruments are connected to the surgical system. Such detection adds to the safety level of the system and provides the user confidence that the instrument being used is functioning properly.

Prior art systems have placed a pressure transducer and associated tubing on the output side of a pneumatic valve. The pneumatic surgical instrument, such as a vitreous (vit) cutter or scissors, is also connected to the output of the pneumatic valve. The pneumatic valve provides pulses of pressurized air for driving the surgical instrument at a desired cut rate. Pressure data from the pressure transducer is used to determine whether the surgical instrument is connected to the pneumatic valve. Connecting the pressure transducer and its tubing to the output of the pneumatic valve adds volume and potentially compliance to the drive line, which in turn, can require greater air pressures and volume to drive the surgical instrument. A pressure transducer connected to the output of the pneumatic valve also complicates and impairs the ability of the valve to drive the surgical instrument at high cut rates, such as rates above 2 k cuts/min by a vit cutter. To minimize the effects of the transducer on the drive line, the transducer size and the diameter of the associated tubing have been minimized as much as possible; this reduced transducer size tends to add cost and limits the available transducer options for manufacturing design. In addition, the transducer is required to be placed very close to the output of the pneumatic valve to provide reliable sensing of air pulses at high cut rates. Requiring the transducer to be close to the valve output reduces options in the design of the pneumatic surgical instrument drive system contained within the surgical system.

Therefore, it would be desirable to eliminate the need for an output-side pressure transducer, yet still provide reliable detection of whether a pneumatic surgical instrument is connected to the surgical system.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
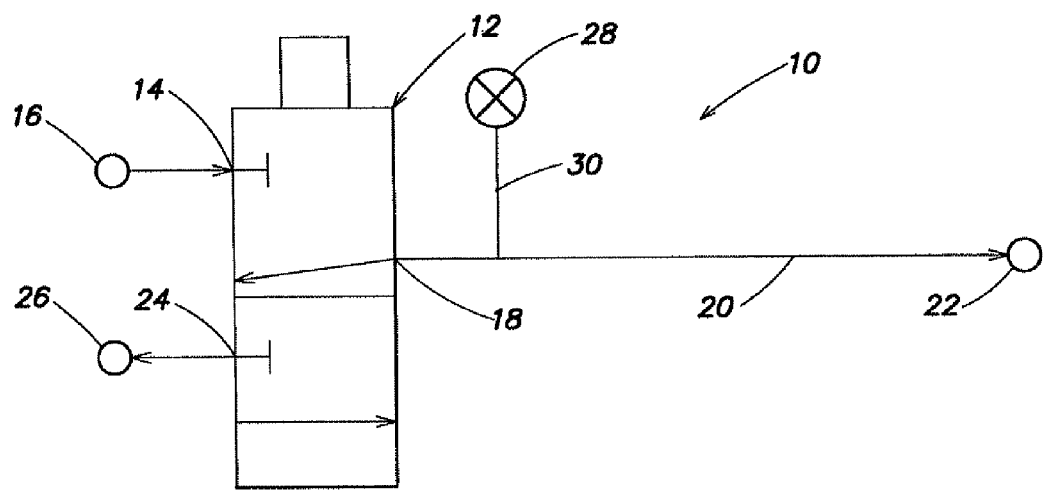
FIG. 1 is a schematic of a prior art instrument detection system.

FIG. 1 is a prior art schematic of a typical instrument detection system 10. System 10 has a 3-way pneumatic valve 12 with an input 14 connected to a source of pressurized air 16, an output 18 connected to a drive-line 20 and a surgical instrument 22, and an exhaust 24 connected to a muffler 26. Drive-line 20 is also connected to a pressure transducer 28 via tubing or line 30. The circuitry associated with detection system 10 is not shown and is of standard design to provide to a central processor (also not shown) a signal indicative of whether surgical instrument 22 is connected to system 10. Once the central processor determines whether surgical instrument 22 is connected to system 10, a surgical system or console (not shown), can take action to disable system 10 and warn the user if instrument 22 is not connected. As discussed above, transducer 28 and line 30 should be placed as close as possible to valve 12, and also be made as small as possible to reduce the volume of air needed between valve 12 and surgical instrument 22.

Figure 2:
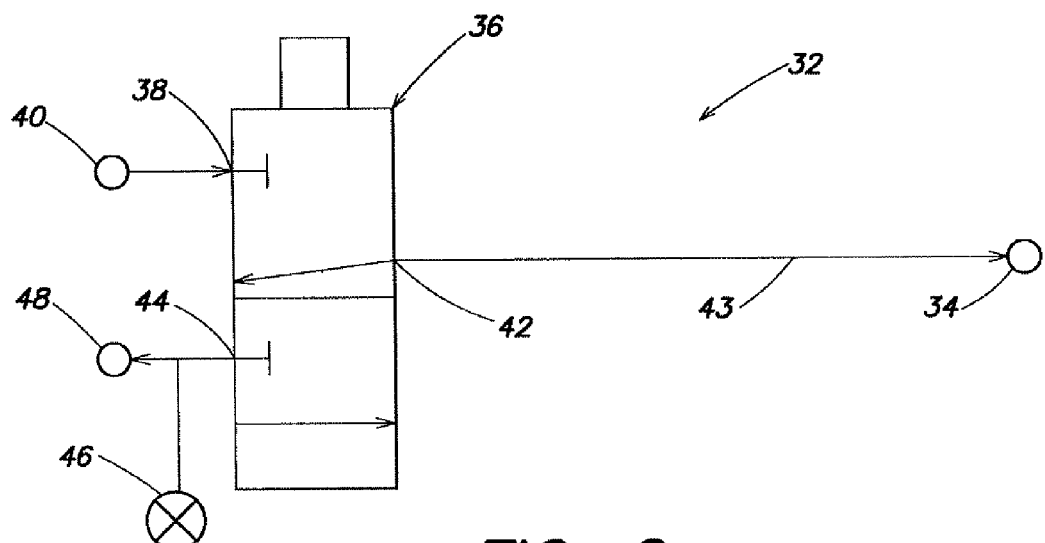
FIG. 2 is a schematic of a surgical instrument detection system, in accordance with a present exemplary embodiment.

An exemplary embodiment of the present disclosure is shown at FIG. 2. A system 32 detects whether a pneumatic surgical instrument 34 is attached to a surgical system (not shown). Pneumatic surgical instrument 34 may be any instrument necessary for surgery, such as a vit cutter or scissors or other instruments driven by pressurized air. System 32 does not show associated circuitry for providing a signal to a central processor of the surgical system; such circuitry can be of conventional design to provide the proper signal to allow the surgical system to control the operation of system 32 and to provide any necessary warnings to a user of the surgical system. The unshown surgical system may be a surgical console that controls several surgical instruments and provides aspiration and irrigation for surgery, or the surgical system may be a stand-alone system that only controls system 32.

System 32 includes a drive valve 36 having an input 38 for connection to a source of pressurized air 40, an output 42 for connection to the surgical instrument 34 via line 43, and an exhaust 44 for exhausting pressurized air during operation of the surgical instrument 34. A pressure transducer 46 is connected in communication with the exhaust 44 for sensing a pressure profile of a flow of air from the exhaust 44. Exhaust 44 may also be connected to a muffler 48 or to the atmosphere. A first sensed pressure profile indicates that the surgical instrument is connected to the output and a second sensed pressure profile indicates that the surgical instrument is not connected to the output. A detection circuit (one example is shown and described below at FIG. 5) is connected to an output of the pressure transducer 46 for detecting whether the surgical instrument 34 is attached to the surgical system based on the sensed pressure profile.

Figure 3:
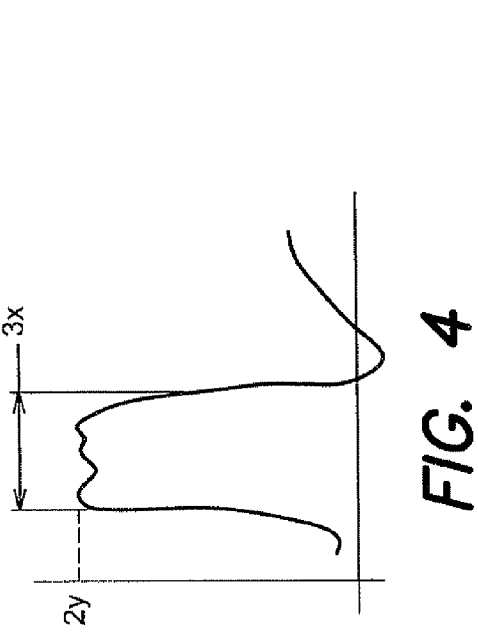
FIG. 3 is an exemplary graph of a sensed pressure profile of FIG. 2, when the surgical instrument is not connected to the system.

FIG. 3 is a graph showing an example of the sensed second pressure profile indicating that the surgical instrument 34 is not connected to the output 42. In the graph, the y-axis is a pressure level and the x-axis is time. It was discovered during development that a distinctive pressure pulse for a given pulse-rate of drive valve 36 can be seen as having a pressure level y for a time x.

Figure 4:
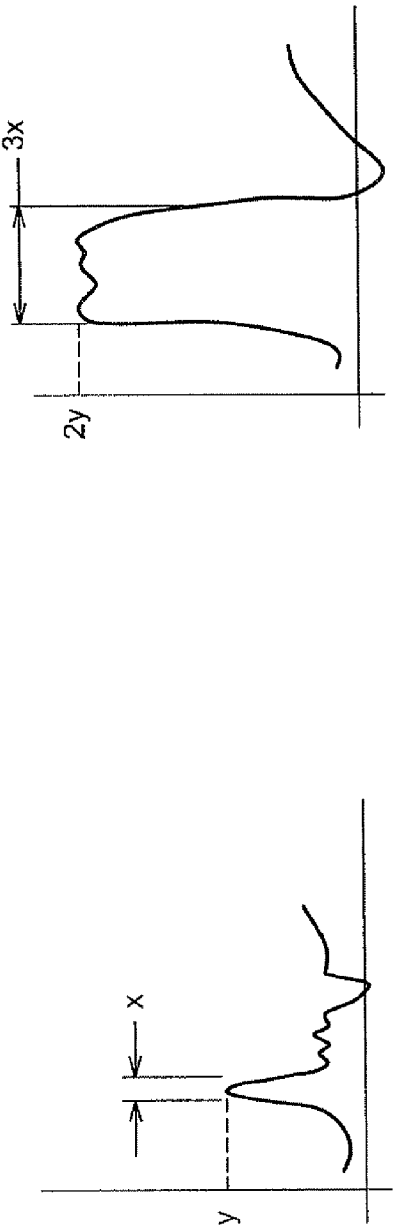
FIG. 4 is an exemplary graph of a sensed pressure profile of FIG. 2, when the surgical instrument is connected to the system.

FIG. 4 is a graph showing an example of the sensed first pressure profile indicating that the surgical instrument 34 is connected to the output 42. As seen, for the same pulse-rate of drive valve 36 as for FIG. 3, a pressure pulse of the first sensed pressure profile was discovered to have a pressure level of 2 y for a time 3 x. Because the first and second pressure profiles can be clearly distinguished, a detection circuit can then be designed to produce a signal indicative of whether the surgical instrument 34 is attached to the output 42.

While FIGS. 3 and 4 show sensed pressure profiles that include exhaust data of pressure over a period of time, it is to be understood that the term "pressure profile" may mean a peak pressure level, a period of time at which a peak or near peak pressure is maintained, or a combination of both.

Figure 5:
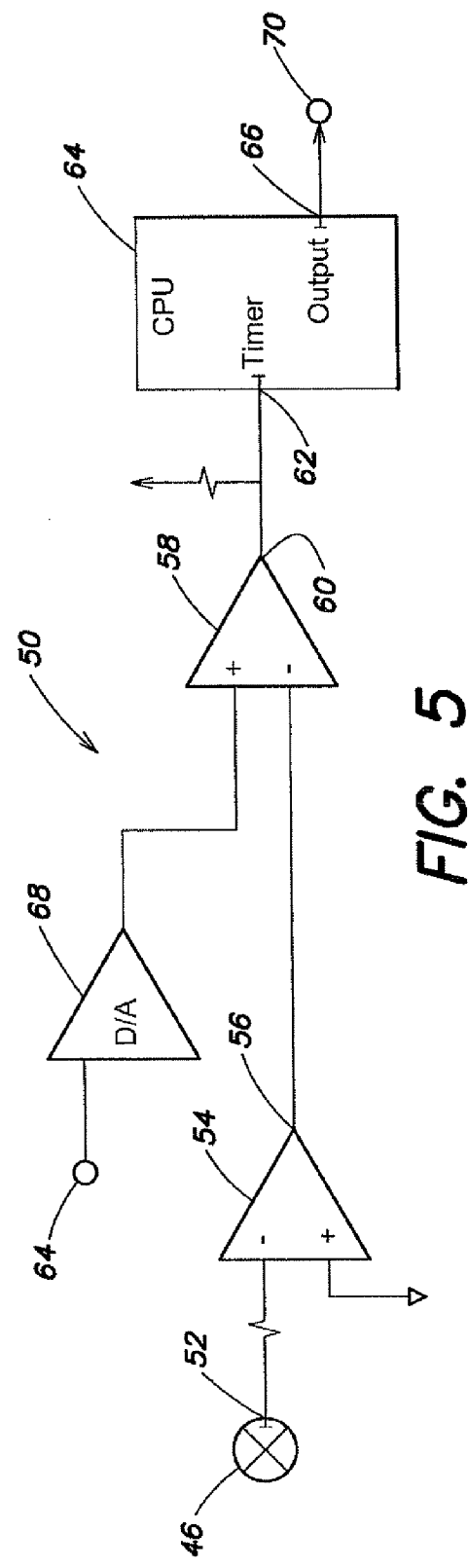
FIG. 5 is a schematic of a portion of a surgical instrument detection system, in accordance with another exemplary embodiment.

FIG. 5 is an example of a detection circuit 50 connected to an output 52 of the pressure transducer 46 for detecting whether the surgical instrument 34 is attached to the surgical system (not shown) based on the sensed pressure profile. Detection circuit 50 may include circuitry for automatically varying a threshold level for determining whether surgical instrument 34 is connected to output 42 based on the cut rate of the surgical instrument 34, as the cut-rate is known by a central processor (CPU) of the surgical system. Detection circuit 50 may include an amplifier 54 connected to the pressure transducer output 52, an output 56 of the amplifier 54 connected to a comparator 58, and an output 60 of the comparator 58 connected to a timer input 62 of a processor 64. A threshold of the comparator 58 may be set to detect the first sensed pressure profile and the processor 64 then produces an appropriate output signal at 66 of the surgical instrument connection status.

A digital to analog (D/A) converter 68 may be connected to comparator 58, as shown, if the threshold level indicating that the surgical instrument 34 is connected to output 42 is to be automatically varied, as described above. D/A convertor 68 is also connected to CPU 64 so that a proper signal level can set the necessary threshold for comparator 58.

Whether D/A convertor 68 is used or not, processor 64 measures or counts how long a pulse remained on and if the on-time is above or below a threshold level. If the on-time is above the threshold level, then the processor can generate a status signal at output 66 indicating that the surgical instrument 34 is connected. Conversely, if the on-time is below the threshold level a signal is generated indicating that surgical instrument 34 is not connected. CPU 64 may be a part of the unshown surgical system.

The detection circuit 50 may further include generating a warning signal to a user when the second sensed pressure profile is detected. The warning signal may be at least one of an audible, a visual, and a tactile signal. The warning signal may be generated at output 66 and may control the operation of portions of the surgical system to generate a warning signal and is represented at 70. Reference number 70 can be any of a number of surgical system components, such as a bell, buzzer, speaker, or voice synthesis device for producing an audible warning signal. Reference number 70 may also be a display for displaying a signal to the user indicating whether the surgical instrument 34 is connected to output 42. Alternatively or additionally, reference number 70 may also be a tactile feedback device such as a vibrating device to provide a tactile signal indicative of whether the surgical instrument 34 is connected to the output 42.

The detection circuit 50 may also include generating a shut-down signal for disabling the drive valve 36 when the second sensed pressure profile is detected.

Figure 6:
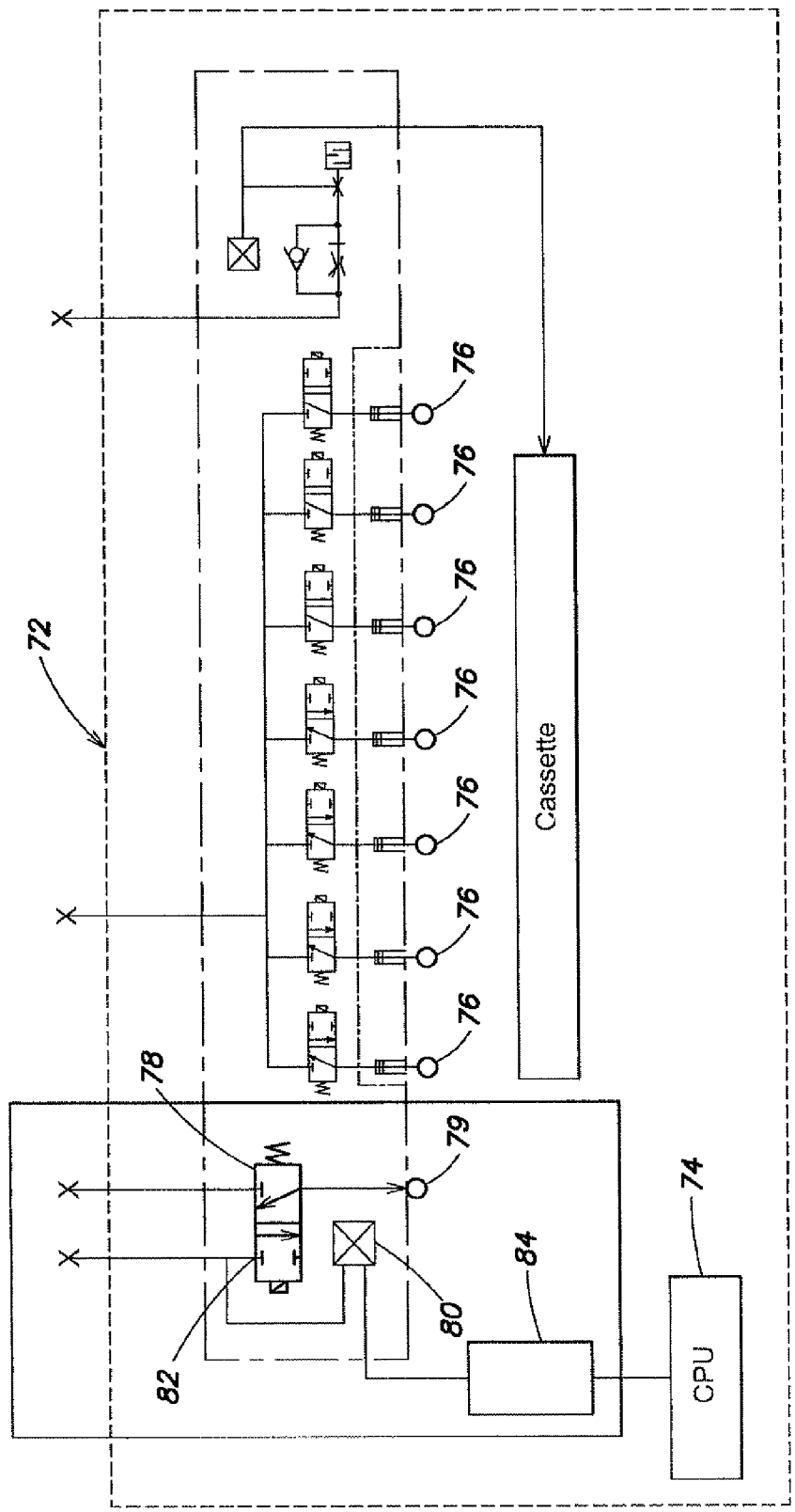
FIG. 6 is a schematic of another exemplary surgical system.

FIG. 6 shows another exemplary surgical system in the context of a complete surgical system. A console 72 has a processor 74 for controlling a variety of instruments and devices (not shown). A plurality of pneumatic valves 76 are connected to the processor 74 (connection not shown for clarity) and includes at least one drive valve 78 for driving a pneumatic surgical instrument 79. A pressure transducer 80 is connected to an exhaust 82 of the drive valve 78. A detection circuit 84 is connected to the pressure transducer 80 for detecting whether the pneumatic surgical instrument 79 is connected to the drive valve 78. The processor 74 receives a signal from the detection circuit 84 indicative of whether the pneumatic surgical instrument 79 is connected to the drive valve 78. The system of FIG. 6 may include the same warnings as described above. Detection circuit 84 may be essentially the same as the detection circuits described above.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

We claim:

1. A system for detecting whether a pneumatic surgical instrument is attached to a surgical system comprising:
    a drive valve having an input for connection to a source of pressurized air, an output for connection to the surgical instrument, and an exhaust for exhausting pressurized air during operation of the surgical instrument;
    a pressure transducer in communication with the exhaust for sensing a pressure profile of a flow of air from the exhaust, wherein a first sensed pressure profile indicates that the surgical instrument is connected to the output and a second sensed pressure profile indicates that the surgical instrument is not connected to the output; and
    a detection circuit connected to an output of the pressure transducer for detecting whether the surgical instrument is attached to the surgical system based on the sensed pressure profile.

2. The system of claim 1, wherein the detection circuit further includes generating a warning signal to a user when the second sensed pressure profile is detected and wherein the warning signal is at least one of an audible, a visual, and a tactile signal.

3. The system of claim 1, wherein the detection circuit further includes generating a shutdown signal for disabling the drive valve when the second sensed pressure profile is detected.

4. The system of claim 1, wherein the detection circuit includes an amplifier connected to the pressure transducer output, an output of the amplifier connected to a comparator, and an output of the comparator connected to a timer input of a processor, wherein a threshold of the comparator is set to detect the first sensed pressure profile.

5. The system of claim 4, wherein the comparator threshold is varied based on a cut-rate of the surgical instrument known by the processor.

6. A surgical system comprising:
a console having a processor for controlling a variety of instruments;
a plurality of pneumatic valves connected to the processor and including at least one drive valve for driving a pneumatic surgical instrument;
a pressure transducer connected to an exhaust of the drive valve for sensing a pressure profile of a flow of air from the exhaust; and
a detection circuit connected to the pressure transducer for detecting whether the pneumatic surgical instrument is connected to the drive valve, wherein the processor receives a signal from the detection circuit indicative of whether the pneumatic surgical instrument is connected to the drive valve.

7. The system of claim 6 further including communicating a warning to a user when the pneumatic surgical instrument is not connected to the drive valve and wherein the warning is at least one of an audible, a visual, and a tactile warning.

8. The system of claim 6 further including generating a shutdown signal for disabling the drive valve when the pneumatic surgical instrument is not connected to the drive valve.

9. The system of claim 6, wherein the detection circuit includes an amplifier connected to the pressure transducer output, an output of the amplifier connected to a comparator, and an output of the comparator connected to a timer input of the processor, wherein a threshold of the comparator is set to detect when the pneumatic surgical instrument is not connected to the drive valve.

10. The system of claim 9, wherein the comparator threshold is varied based on a cut-rate of the pneumatic surgical instrument known by the processor.

* * * * *